(12) United States Patent
Owen et al.

(10) Patent No.: US 10,390,746 B2
(45) Date of Patent: Aug. 27, 2019

(54) CATHETER

(75) Inventors: Richard Harley Grenville Owen, Huntington (GB); Stephen Blatcher, Duxford (GB); Stewart Maddison Fox, Cambridge (GB); Martin Lawrence Hughes, Wavendon (GB)

(73) Assignee: PLAQUETEC LIMITED, London (GB)

(*) Notice: Subject to any disclaimer, the term of this patent is extended or adjusted under 35 U.S.C. 154(b) by 2631 days.

(21) Appl. No.: 11/920,632

(22) PCT Filed: May 25, 2006

(86) PCT No.: PCT/GB2006/001933
§ 371 (c)(1),
(2), (4) Date: Dec. 21, 2007

(87) PCT Pub. No.: WO2006/126002
PCT Pub. Date: Nov. 30, 2006

(65) Prior Publication Data
US 2009/0024057 A1    Jan. 22, 2009

(30) Foreign Application Priority Data
May 26, 2005 (GB) .................... 0510801.4

(51) Int. Cl.
*A61B 5/155* (2006.01)
*A61B 5/15* (2006.01)
(Continued)

(52) U.S. Cl.
CPC .......... *A61B 5/155* (2013.01); *A61B 1/00094* (2013.01); *A61B 5/15003* (2013.01);
(Continued)

(58) Field of Classification Search
CPC . A61B 5/1427; A61B 5/1468; A61B 5/14542; A61B 5/14539; A61B 5/14503;
(Continued)

(56) References Cited

U.S. PATENT DOCUMENTS 3,384,170 A * 5/1968 Van Poollen ................. 166/264
3,595,241 A   7/1971 Sheridan
(Continued)

FOREIGN PATENT DOCUMENTS

GB    1 405 556       9/1975
GB    2 003 388 A    3/1979
(Continued)

OTHER PUBLICATIONS

Office action dated May 19, 2014 issued in connetion with U.S. Appl. No. 13/105,726.
(Continued)

*Primary Examiner* — Adam J Eiseman
(74) *Attorney, Agent, or Firm* — Foley & Lardner LLP

(57) ABSTRACT

A catheter for insertion into a blood vessel, the catheter having a sampling part arranged to capture a blood sample at a plurality of locations along a length of the blood vessel and an apparatus arranged to analyze blood taken from a plurality of locations along the length of the blood vessel and to provide a profile of concentration levels along the length of the blood vessel.

20 Claims, 15 Drawing Sheets

(51) Int. Cl.
*A61B 5/153* (2006.01)
*A61B 5/154* (2006.01)
*A61M 25/00* (2006.01)
*A61B 1/00* (2006.01)

(52) U.S. Cl.
CPC .............. *A61B 5/153* (2013.01); *A61B 5/154* (2013.01); *A61B 5/150236* (2013.01); *A61B 5/150992* (2013.01); *A61M 25/0071* (2013.01); *A61M 2025/0008* (2013.01)

(58) Field of Classification Search
CPC . A61B 5/145; A61B 1/00094; A61B 10/0283; A61B 2010/0225; A61B 5/15003; A61B 5/150236; A61B 5/150992; A61B 5/153; A61B 5/154; A61M 25/0068; A61M 25/007; A61M 25/0071
USPC ........ 600/573, 575–576, 578–579, 581–582, 600/584; 604/523, 532, 537
See application file for complete search history.

(56) References Cited

U.S. PATENT DOCUMENTS

| | | | |
|---|---|---|---|
| 4,072,146 A * | 2/1978 | Howes | 600/487 |
| 4,265,249 A | 5/1981 | Schindler et al. | |
| 4,445,788 A * | 5/1984 | Twersky et al. | 374/142 |
| 4,573,968 A | 3/1986 | Parker | |
| 4,638,811 A | 1/1987 | Bisera et al. | |
| 4,643,712 A * | 2/1987 | Kulik et al. | 604/6.16 |
| 4,753,640 A * | 6/1988 | Nichols et al. | 604/247 |
| 4,787,882 A * | 11/1988 | Claren | 604/6.16 |
| 4,808,158 A | 2/1989 | Kreuzer | |
| 5,066,283 A | 11/1991 | Skrabal | |
| 5,078,135 A | 1/1992 | Caprioli | |
| 5,472,417 A * | 12/1995 | Martin et al. | 604/43 |
| 5,531,714 A | 7/1996 | Dahn et al. | |
| 5,533,516 A | 7/1996 | Sahatjian | |
| 5,702,418 A | 12/1997 | Ravenscroft | |
| 6,165,199 A * | 12/2000 | Barbut | 606/200 |
| 6,607,477 B1 | 8/2003 | Longton et al. | |
| 7,179,232 B2 * | 2/2007 | Sutton et al. | 600/567 |
| 2002/0107479 A1* | 8/2002 | Bates et al. | 604/96.01 |
| 2003/0171664 A1 | 9/2003 | Wendlandt | |
| 2003/0208154 A1 | 11/2003 | Close et al. | |
| 2005/0038411 A1* | 2/2005 | Okada | A61L 29/049 604/523 |
| 2007/0232981 A1* | 10/2007 | Ravenscroft et al. | 604/6.16 |

FOREIGN PATENT DOCUMENTS

| | | |
|---|---|---|
| JP | 54-026783 | 2/1979 |
| JP | 62-079069 | 4/1987 |
| WO | WO 02/083228 A2 | 10/2002 |
| WO | WO 03/080166 A1 | 10/2003 |
| WO | WO 2004/010874 A1 | 2/2004 |

OTHER PUBLICATIONS

Office Action in JP 2008-512921 dated Apr. 3, 2012.
Office Action in U.S. Appl. No. 13/105,726 dated Mar. 16, 2012.
Office Action in U.S. Appl. No. 13/105,726 dated Sep. 25, 2012.

* cited by examiner

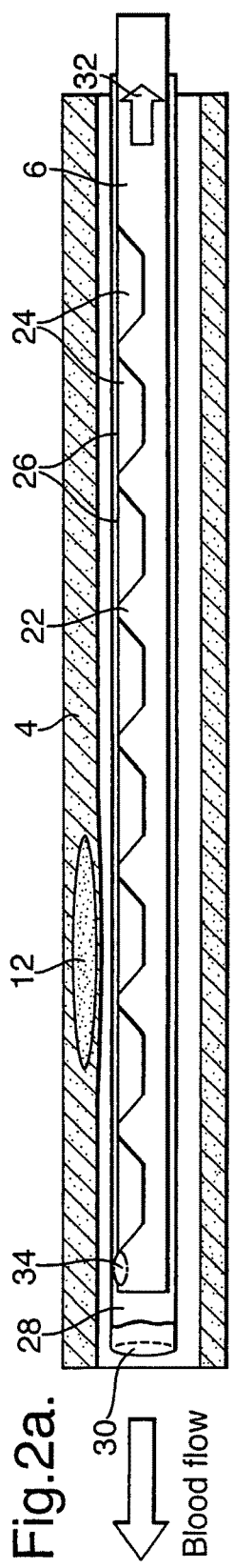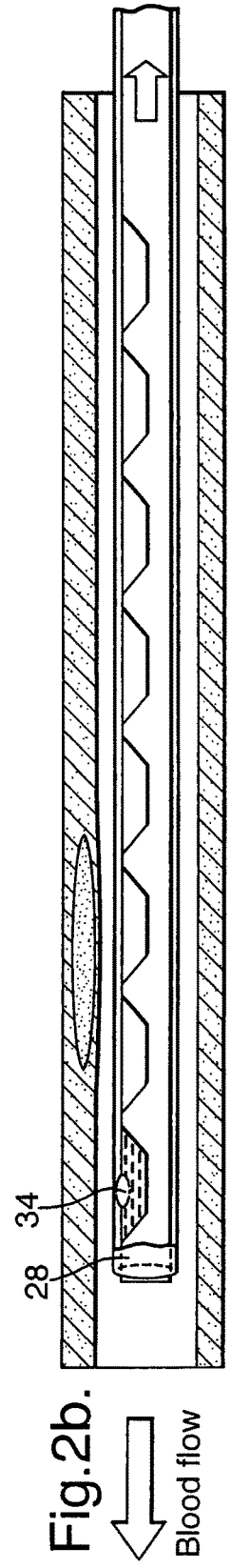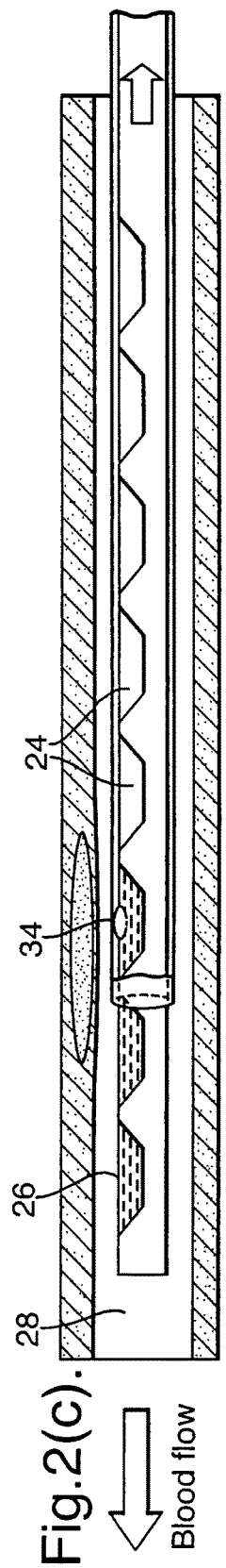

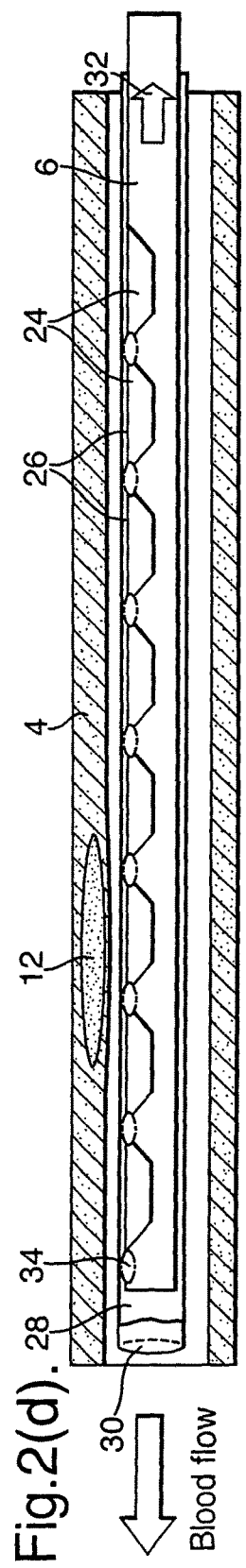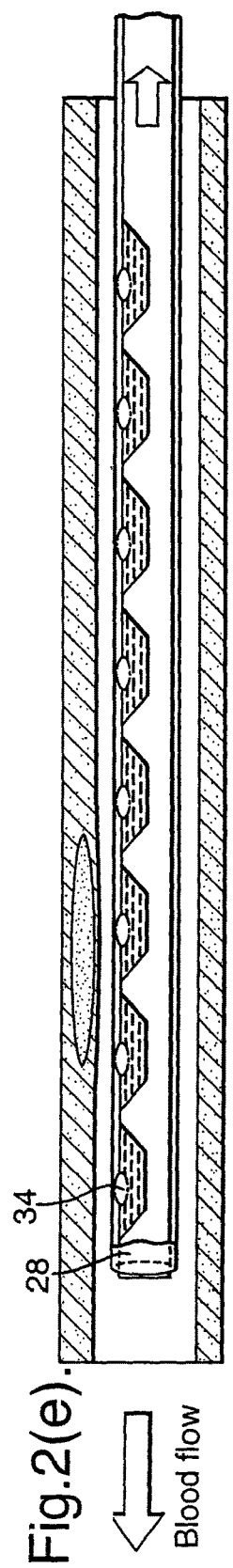

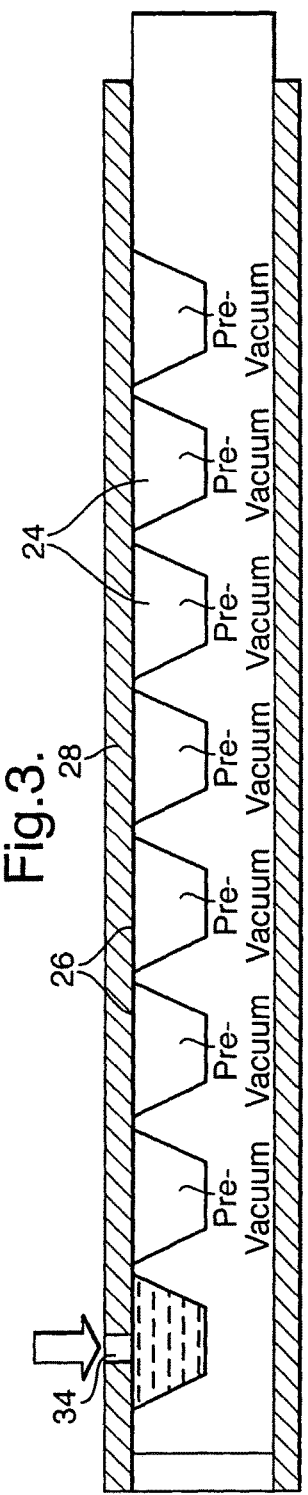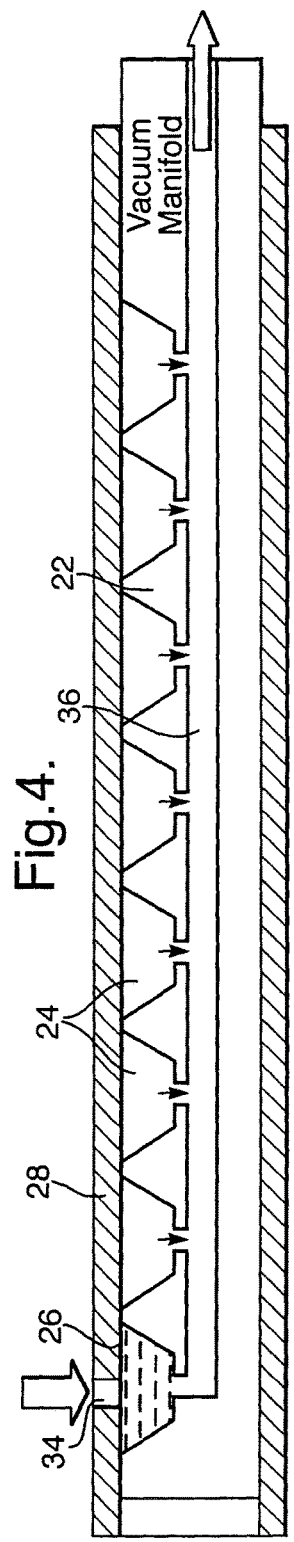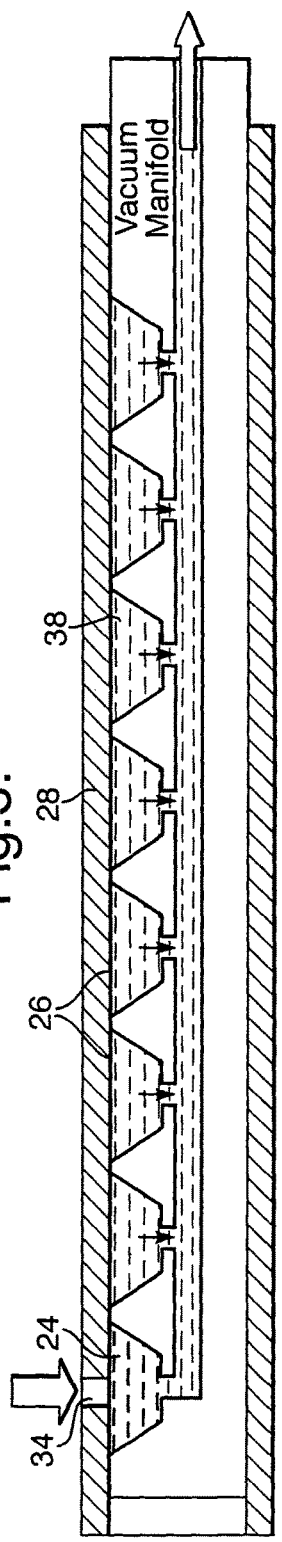

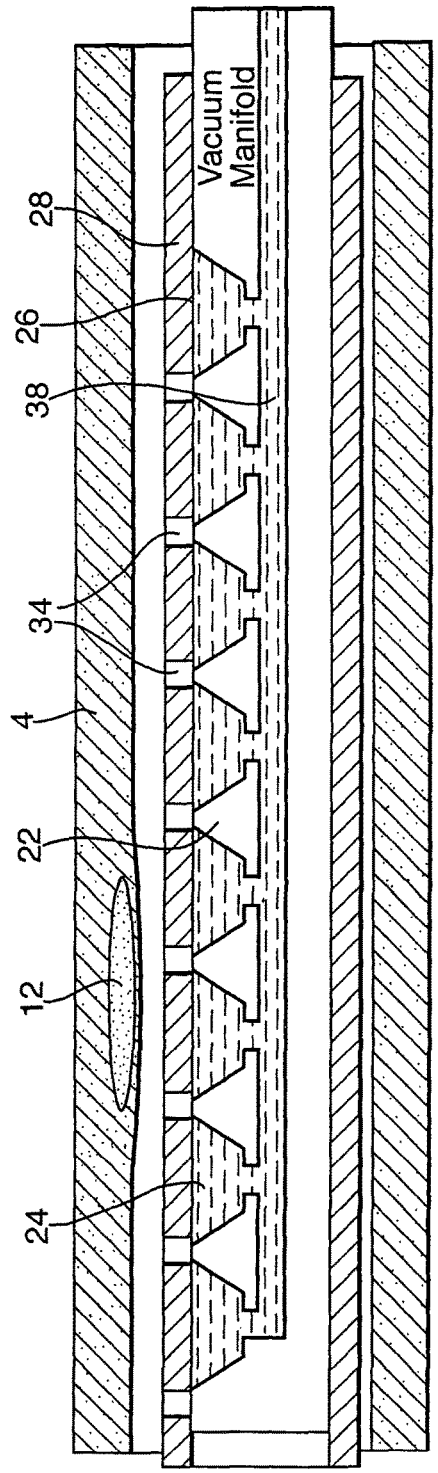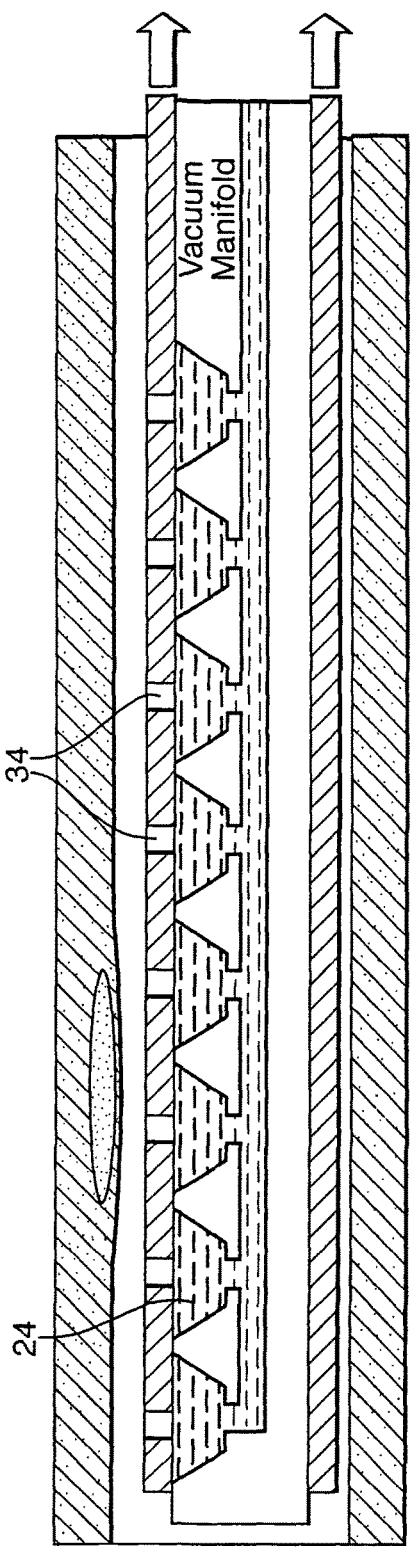

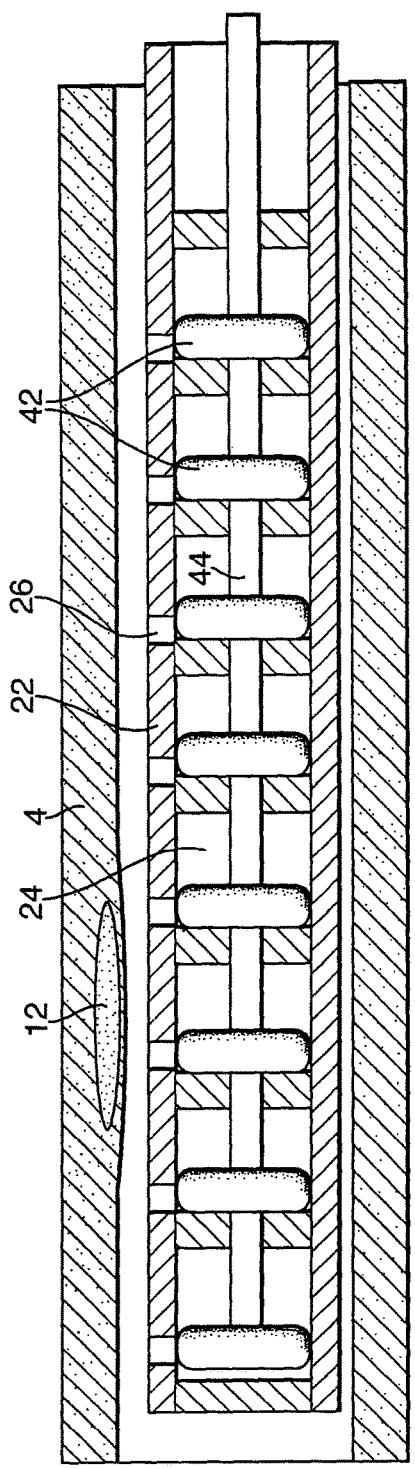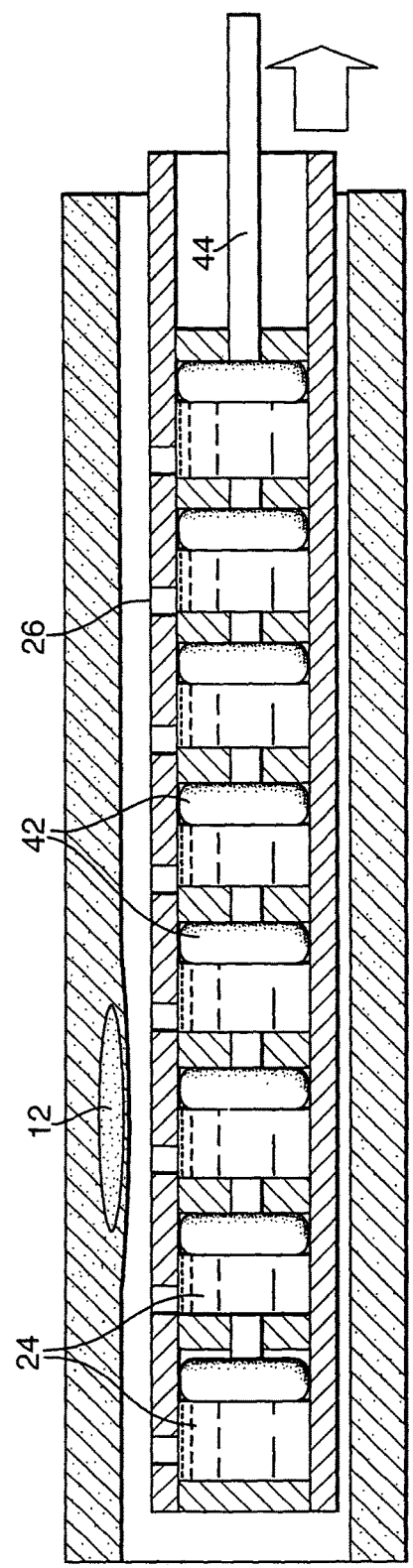

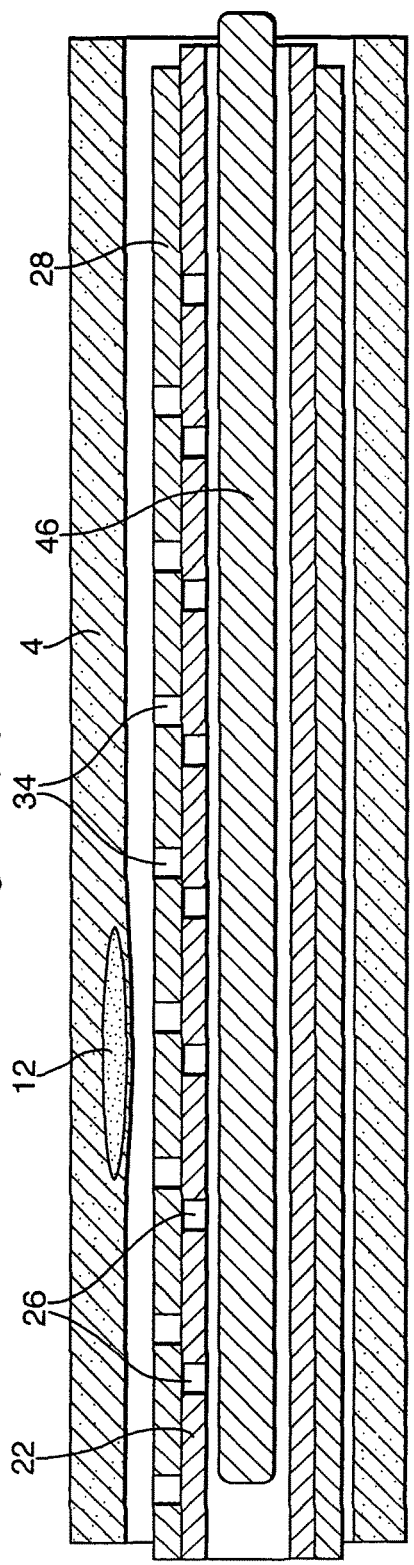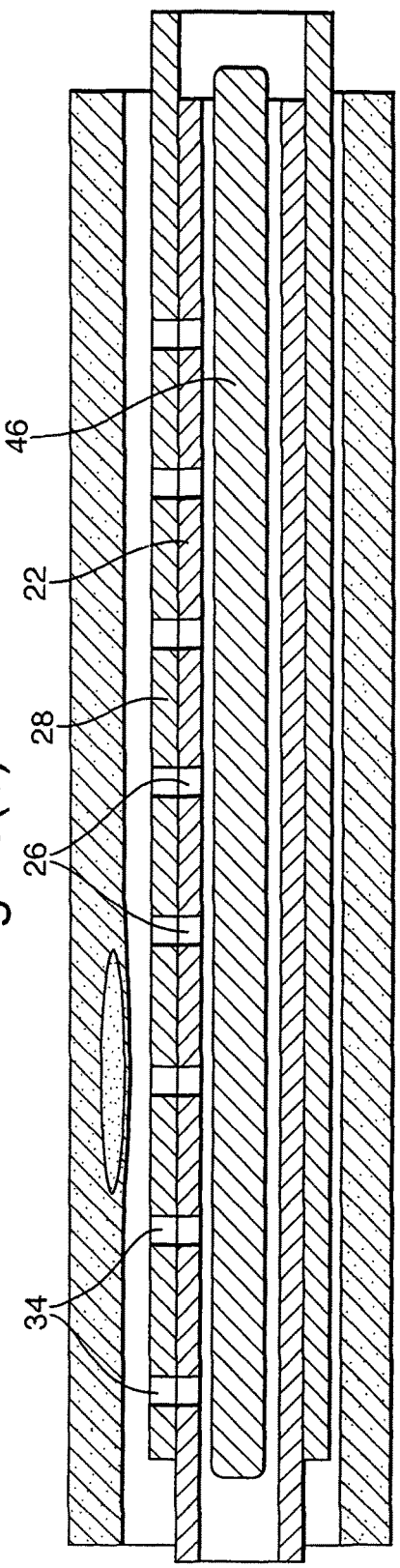

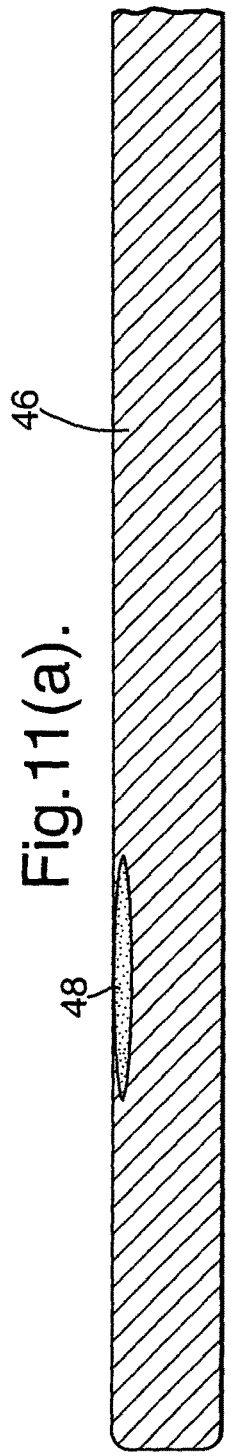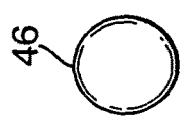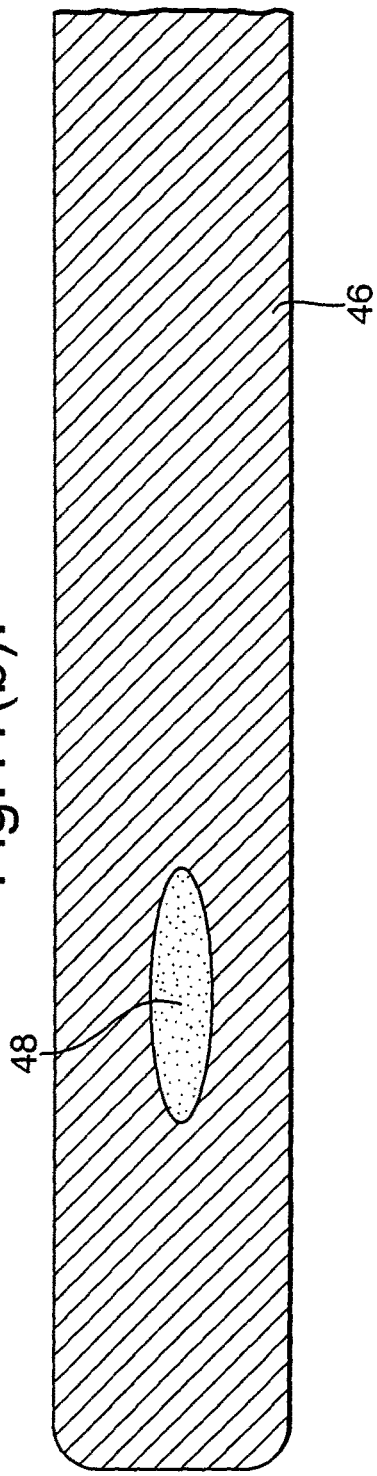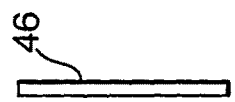

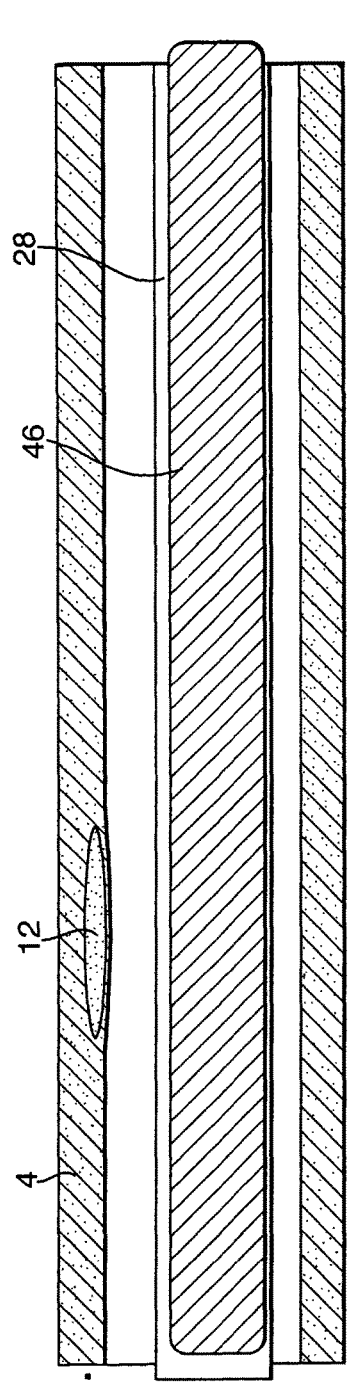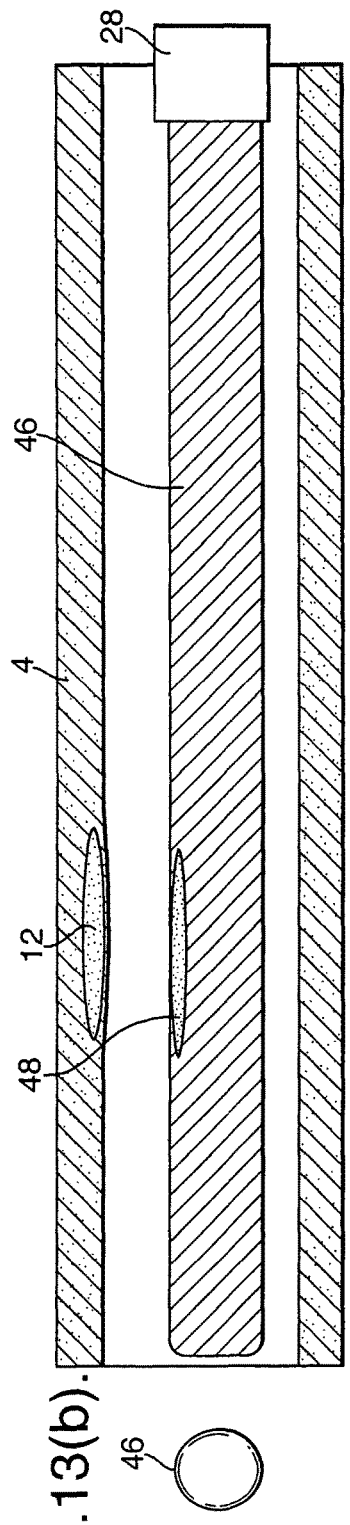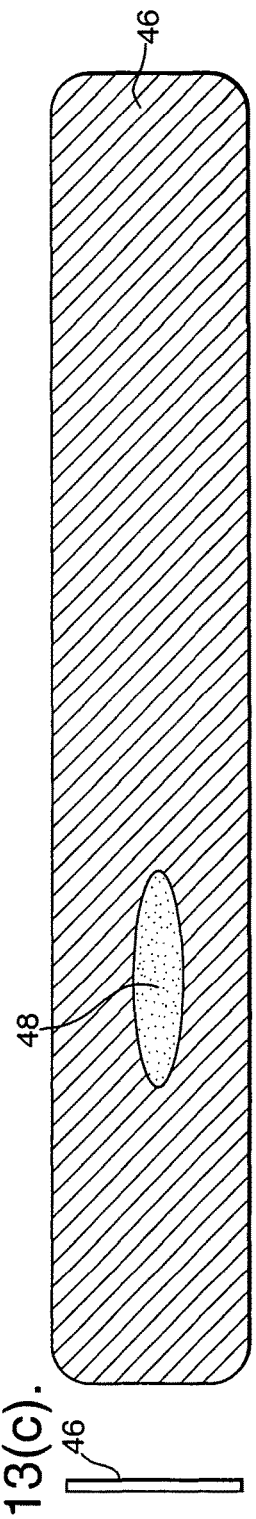

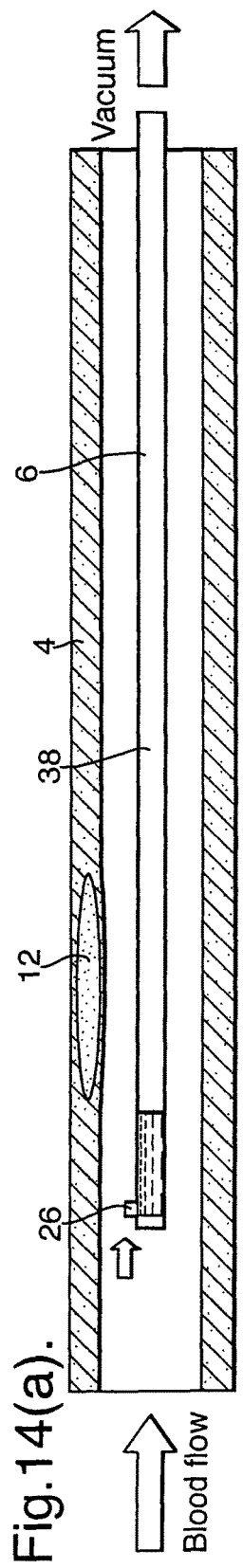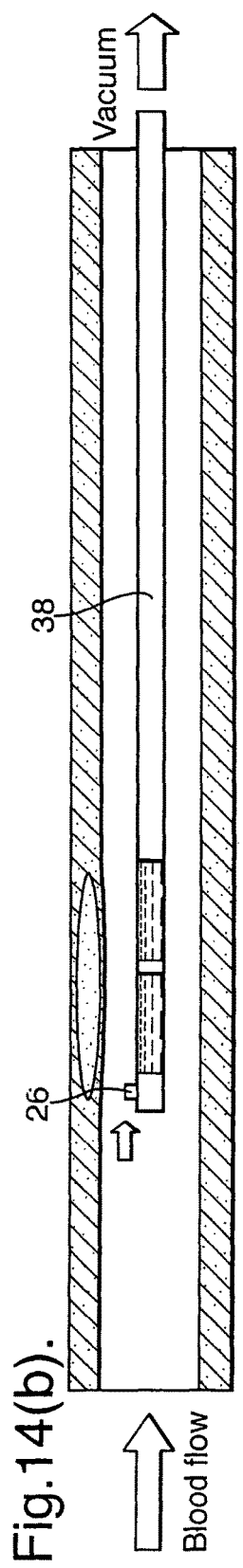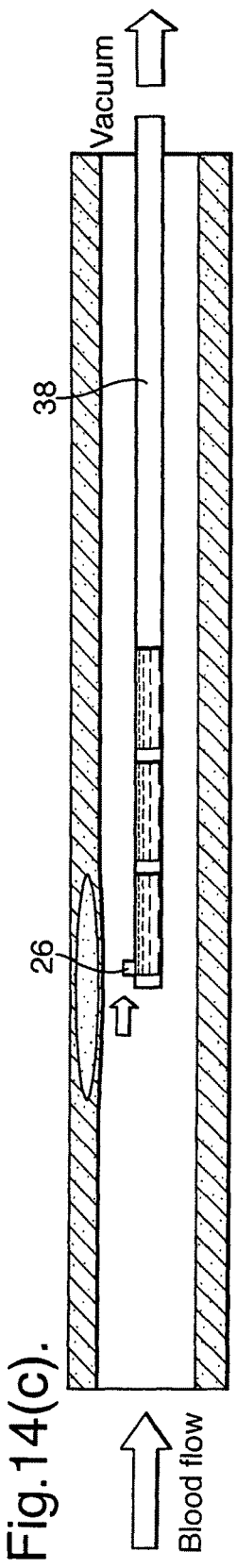

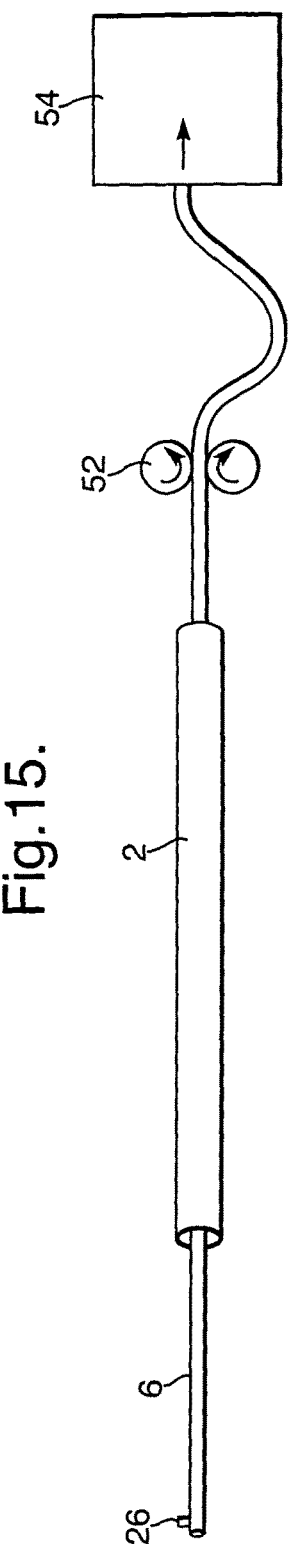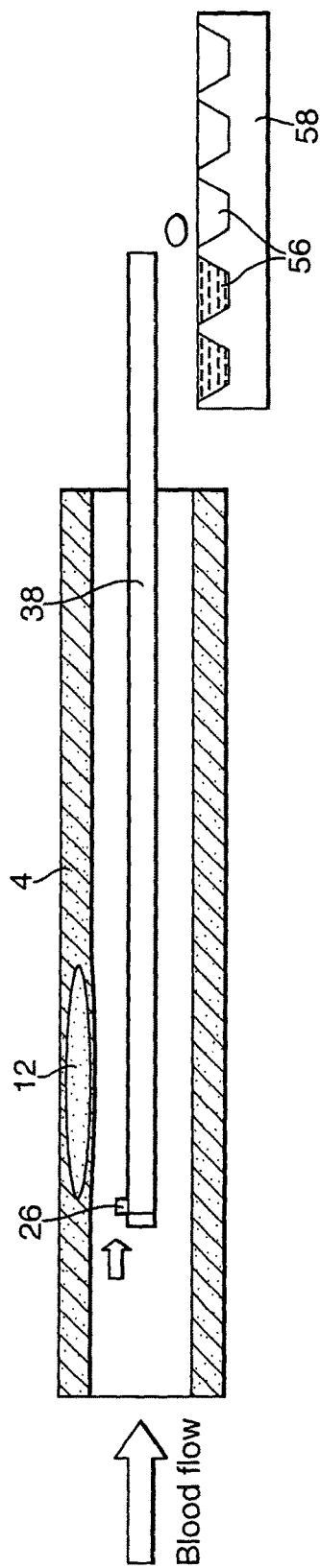

CATHETER

The present invention relates to a catheter and also an apparatus for use with that catheter and a system including the catheter and apparatus. In particular, it relates to a catheter for insertion into a blood vessel allowing blood samples to be taken.

BACKGROUND

It is known, for instance, from US 2004/0102686 to carry out methods of diagnosis for identifying vulnerable plaque by identifying pathological markers such as C-reactive protein or pH change generated by the pathological site. US 2004/0102686 describes an arrangement where first and second detectors are advanced through a blood vessel with each of the detectors selected to detect the pathological marker. The detectors are spaced axially apart such that differential concentration of the pathological marker as measured by the detectors indicates the presence of the pathological site in proximity to at least one of the detectors. The use of detectors in this way is somewhat limiting and relatively expensive. Specific detectors have to be provided for respective tests, fitting these detectors in the catheter is relatively difficult and, where a variety of different catheters are provided, each requires separate regulatory approval. Furthermore, the spacing of the detectors is such that any markers for detection have been diluted throughout the blood volume such that their concentration is significantly affected by the general background level and it becomes more difficult accurately to identify the source of the markers.

U.S. Pat. No. 5,533,516 describes taking a bodily sample, e.g., a cell sample, from deep within the body of a patient and collecting the sample outside the body to facilitate treatment of the patient. A sampling probe is provided in the form of an elongate catheter having a proximal portion that remains outside the body and a distal portion that can be located within the body. The distal portion includes a membrane with openings that communicate with space that communicates with a source of suction force. The catheter is positioned within the body. The sample is taken by exposing the membrane by placing it in proximity with a desired location so that the bodily sample is received by the membrane. The catheter is removed from the patient, the sample is collected outside the body, treated, disposed onto a device, such as a graft, stent, or catheter, and reintroduced into the body at a desired site.

GB 1 405 556 describes an endometrial sampler, comprising a hollow tube having a sampling end containing a plurality of sampling ports communicating with the interior of the tube, and a sleeve surrounding the tube and slidable with respect to it, the sleeve and the tube being reciprocable with respect to one another between a sampling position in which the sleeve exposes at least one of the sampling ports and a second position in which the sleeve engages a forward stop on the tube and covers all the sampling ports.

SUMMARY

It is an object of the present invention to provide an improved means of diagnosis whilst at least reducing the problems mentioned above.

The present invention provides a method of providing a data profile, optionally as part of a method of diagnosis, whereby a blood sample is taken at a plurality of locations along a length of a blood vessel so as to provide a profile of concentration levels along that length of the blood vessel.

It is possible to collect multiple, spatially separated samples at a single instance in time (eg via multiple sheath holes), these remaining separated with no mixing. Individual collection ports can be ejected into multiple sample chambers for analysis.

Having taken blood samples in this way, it is possible to apply a variety of tests to the blood so as to provide profiles relating to any desired tests. For instance, the profiles could relate to C-reactive protein, heat-shock proteins, hydrogen ion concentration (pH), cholesterol, cells, cell surface markers, etc. By means of the profile, any background levels in the sample of blood may be calculated and the location of any problem areas may be accurately determined.

Preferably, the method involves obtaining the blood samples using a catheter which is inserted into the blood vessel at a known position, such that treatment of an identified problem area may be applied accurately with reference to the known position of the diagnostic catheter. In this way, it becomes very easy for a clinician to perform diagnosis of the blood vessel and then apply treatment specifically to the identified problem area.

According to the present invention there is provided a catheter for insertion into a blood vessel, the catheter having a sampling part arranged to capture a blood sample at a plurality of locations along a length of the blood vessel.

The catheter can preserve the spatial separation of samples collected at a single instance in time.

In this way, a catheter of this type can be used to conduct a number of different tests. Indeed, such tests may even be carried out simultaneously. As a result of the tests on the sample of blood, a profile of concentrations in the blood may be provided so as to enable problem areas in the blood vessel to be identified.

In general, the catheter will be arranged to capture a blood sample at at least three locations along the length of the blood vessel, but, preferably at at least five locations if not 20, 100 or more. It is considered that samples might be taken over a length of perhaps 100 them. It is envisaged that the catheter captures blood samples at locations every 1 them along the length or even closer, for instance 0.5 them. The catheter has the potential to sample nano to micro liter volumes.

By collecting samples at multiple locations from inside the blood vessel, true background levels in the serum can be found (upstream of the source). Furthermore, the marker can be detected at a higher local concentration, because it will be collected nearer the source before it is diluted. Also, as mentioned above, the source of the marker can be located more accurately by virtue of the number of samples collected along the length of the blood vessel.

Since the marker can be detected at a higher local concentration, the levels of the marker can be determined more sensitively. In particular, the level of the marker will be higher in relation to the background level. Hence, the marker can be detected even if the patient has an elevated background level of inflammatory marker.

The arrangement allows future coronary events to be predicted more accurately so that patients at severe risk of MI (myocardial infarction) and/or stroke can monitored or given prophylactic treatment. Also, low risk patients can be identified more accurately and managed more economically than previously.

Unstable plaques in the blood vessel can be located accurately which allows targeted local therapy, such as stenting.

With the arrangement of the present invention, the progress/effectiveness of chemical therapy can be monitored in more detailed than before. Furthermore, the process is compatible with clinical procedures as the catheter could collect samples within blood vessels during routine exploratory procedures. The process is compatible with clinical budgets, since the catheter of the present invention is relatively straightforward to construct and, hence, relatively inexpensive.

It is not necessary for the catheter to contact the vessel wall or to use suction to pull the vessel wall to the device. Indeed, it is preferred not to. It is preferred not to damage the endothelium (inner wall of artery) and to collect blood and biological samples in close proximity to the wall.

Preferably, the sampling part includes an axially elongate sample member having an axial array of a plurality of openings for receiving blood from outside the catheter at intervals along said length of the blood vessel.

In this way, each of the openings collects a sample of blood from a different location along the length of the blood vessel. The openings may be arranged to collect samples one after the other or, alternatively, at the same time.

Preferably, the sampling part includes an elongate sleeve coaxial with the sample member and defining an axial passage for housing the sample member wherein relative movement of the sleeve axially along the sample member exposes the openings so as to collect a respective plurality of samples along said length of the blood vessel.

In this way, the openings may be kept closed by the sleeve until the catheter is located at a desired position. Although this is highly advantageous in some embodiments, where blood samples are actively drawn into individual openings, it may not be necessary.

The sleeve can include a plurality of respective through-holes positioned so that all of the openings may be exposed simultaneously to blood outside the catheter.

In other words, the through-holes are arranged in an array corresponding to the array of openings. At first, the through-holes are out of alignment with the openings, but movement of the sleeve relative to the sample member brings the through-holes into alignment with the openings.

Preferably, the sampling part includes a respective plurality of pockets for receiving blood from the openings.

In this way, the pockets provide respective storage chambers for each opening.

Preferably, each of said pockets is at least partially evacuated such that, upon exposure by the sleeve, the pockets suck in blood from outside the catheter.

The sleeve thus seals the opening and pockets so as to maintain a low pressure (relative to atmosphere) in the pockets whilst the catheter is positioned in the blood vessel. When the sleeve is moved to expose the pockets, the low pressure draws in blood from outside the catheter.

Alternatively, the sampling member may include a vacuum passageway connecting each of the pockets, the vacuum passageway allowing suction to be applied to each of the pockets.

In this, way, by connecting the vacuum passageway to an external low pressure source, blood samples may be drawn through the openings as required.

The pockets and the vacuum passageway may be pre-filled with a fluid, such as saline, which can be drawn out of the catheter so as to draw blood into the pockets from outside the catheter.

Pre-filling the pocket and vacuum passageway in this way, as with evacuating the pockets, reduces the release of bubbles into the blood flow.

As an alternative, the sampling part may include a respective plurality of vacuum passageways connected to respective openings so as to allow suction to be applied individually to each opening.

In this way, sampling from each opening can be individually controlled.

The catheter may further include a respective plunger within the or each vacuum passageway moveable away from the openings so as to draw blood through the openings from outside the catheter.

It will be appreciated that movement of the plunger in a vacuum passageway will cause blood to flow into the respective opening. Where the openings are provided with individual respective vacuum passageways and plungers, the samples taken by those openings can be individually controlled.

The sampling part may further include a respective plurality of pistons in the pockets whereby movement of the pistons away from the respective openings sucks blood into the respective pockets.

The pistons act like the plungers mentioned above, but are provided within pockets, rather than the vacuum passageways.

Preferably, the pistons are moveable in the axial direction to suck blood into the respective pockets and the sampling part further includes an axially extending actuator to which all of the pistons are attached and by which the pistons may be moved.

This provides a convenient arrangement for simultaneously actuating the pistons of all of the pockets.

A membrane layer may be provided covering the openings, the membrane layer allowing plasma through the openings.

In this way, plasma may be sampled whilst leaving platelets etc outside the catheter. This increases the concentration of the test sample and allows reduction in the collection volume.

As described above, preferably, the sampling part is arranged to capture a plurality of discrete samples along said length of the blood vessel. Many diagnostic chemistry processes require samples of approximately 50 µl and, hence, for many embodiments each discrete sample is substantially of this value. However, the discrete samples may be between 0.1 µl and 100 µl, more preferably between 20 µl and 50 µl.

The sampling part may include an axially elongate sample member comprising a continuous absorbent material. This can be used in conjunction with the axial array of openings, such that each opening feeds a respective sample into a respective part of the same continuous absorbent material. A sleeve may be used in conjunction with this. Alternatively, however, the continuous absorbent material may be provided so as to continuously sample blood along its length. Again, a sleeve may be provided to control exposure of the material to the blood outside the catheter. The sample member can be directly analysed to measure differences in samples along the length of the device.

The catheter may be provided with an inlet port at a distal end of the sampling part and an outlet port at a proximal end of the sampling part, the sampling part defining an axial channel running from the distal end to the proximal end, and a suction device for connection to the outlet part and a positioning device at the proximal end, the suction device being arranged to draw blood in the inlet port and the positioning device being arranged to move the sampling part and, hence, move the inlet port along said length of the blood vessel.

Accordingly, a method of provided whereby blood is drawn into a single inlet port of the catheter whilst that inlet port is moved along a predetermined length of the blood vessel.

In this way, the continuous sample of blood drawn into the catheter represents a sample along the length of the blood vessel.

The catheter may be provided with a sample collector in fluid communication with the outlet port for collecting consecutive samples from the inlet port.

In other words, the blood flow from the inlet port as collected at the outlet port is divided into discrete samples which represent discrete samples along the length of the blood vessel.

Preferably, the catheter includes a reference guide for insertion into a blood vessel at a fixed position relative to the blood vessel, the reference guide defining an axial duct into which the sampling part may be inserted to collect blood samples and from which the sampling part may be extracted, the reference sleeve and the sampling part being provided with respective indexing parts which position the sampling parts at a predetermined relative position with the reference sleeve when the sampling part is inserted in the axial duct.

In this way, any results of analysing the blood sample taken by the catheter can be considered with reference to positions located accurately with reference to the reference guide. By leaving the reference guide in place whilst carrying out any tests on the blood sample, it becomes easy for a clinician then accurately to position any treatment.

In this respect, the catheter preferably further includes a treatment part for insertion into the axial duct in place of the sampling part, the treatment part having an indexing part allowing, by reference to the indexing part of the reference guide, the treatment part to be positioned in the blood vessel as required.

Hence, it is easy to position any required treatment along the length of the blood vessel accurately with reference to results from the test on the blood sample.

The present invention also provides an apparatus for analysing blood samples captured by a catheter as described above, the apparatus being arranged to analyse blood taken from a plurality of locations along said length of the blood vessel and to provide a profile of concentration levels along said length of the blood vessel.

The apparatus is preferably arranged to provide a profile of cardiac inflammatory marker along the length of the blood vessel.

It is preferably further arranged to calculate from the profile the marker background level of the sample of blood.

It is preferably further arranged to predict, from elevated portions of the profile, the location of problem areas along the length of the blood vessel.

According to the present invention, there is also provided a catheter system including both the catheter and the apparatus described above.

By means of the present invention, gradients can be measured by collecting separate samples of whole blood at multiple locations in a linear path along the longitudinal axis of the blood vessel. Either at the time of collection or immediately after collection, the samples from different locations are kept as separate discrete entities. The collected samples are extracted from the body and analysed using, for instance, antibody-based methods to determine the concentration of inflammatory marker(s) in each separate sample. The concentration of the markers can be plotted against their location along the length of the sampling catheter.

The catheter may take samples not only along the length of the blood vessel, but also radially around the outer periphery of the catheter. In this case, the concentration markers can be plotted against their location in three dimensions.

The plot can be referenced to the precise position in the blood vessel where the samples were taken. This may be determined by X-ray/fluoroscopy or merely with reference to the reference guide as described above. This shows the gradient of the markers as the rate of change of concentration along the length of the blood vessel. The gradient can be used to determine the markers more sensitively than with previous techniques and can locate vulnerable plaques allowing the potential of targeted local therapy, e.g. stenting, as described above.

The catheter can be used in combination with other diagnostic and imaging devices and systems incorporating acoustic (e. g. Intravascular Ultrasound IVUS, etc.) and/or electromagnetic sensing/imaging modalities (e. g. Optical coherence tomography, Angioscopy, Thermography, Spectroscopy, Magnetic Resonance Imaging, Electron beam computed tomography, etc.). Hybrid devices can be provided with combined sensing platforms in a single device e. g. a catheter according to the present invention with an IVUS probe at the end. The advantage of combined devices is that it would enable clinicians to use a single procedure to examine the vessels with a familiar technique, such as IVUS, and, in areas of concern, collect blood using the catheter of the present invention.

It will be appreciated that, although the catheter has been described with reference to its use in a blood vessel, it can also be used inserted into other parts of the body.

BRIEF DESCRIPTION OF THE DRAWINGS

The invention will be more clearly understood from the following description given by way of example only, with reference to the accompanying drawings, in which:

FIGS. 2(a), (b) and (c) illustrate a catheter;

FIGS. 2(d) and (e) illustrate a catheter embodying the present invention;

FIG. 3 illustrates a catheter embodying the present invention;

FIG. 4 illustrates a catheter embodying the present invention;

FIG. 5 illustrates a catheter embodying the present invention;

FIGS. 7(a) and (b) illustrate a catheter embodying the present invention;

FIGS. 9(a) and (b) illustrate a catheter embodying the present invention;

FIGS. 10(a) and (b) illustrate a catheter embodying the present invention;

FIGS. 11(a) and (b) illustrate an absorbent planar member; and

FIGS. 13(a), (b) and (c) illustrate a catheter embodying the present invention;

FIGS. 14(a), (b) and (c) illustrate a catheter embodying the present invention;

FIG. 15 illustrates a catheter embodying the present invention with a positioning device and a suction device; and FIG. 16 illustrates a catheter embodying the present invention with a sample collector.

DETAILED DESCRIPTION

Figure 1A:
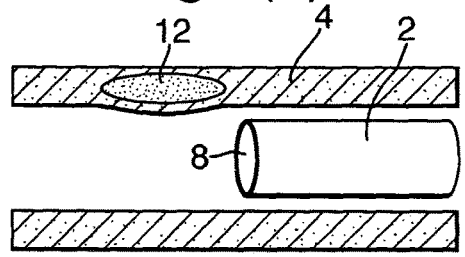
FIGS. 1(a) to (g) illustrate schematically a general method of treatment and diagnosis.
Figure 1B:
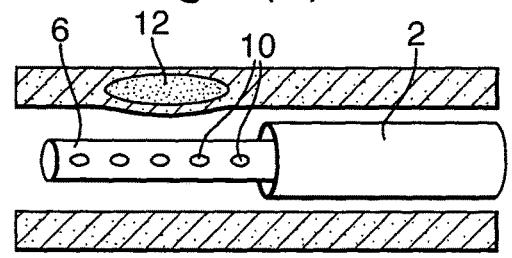
Figure 1C:
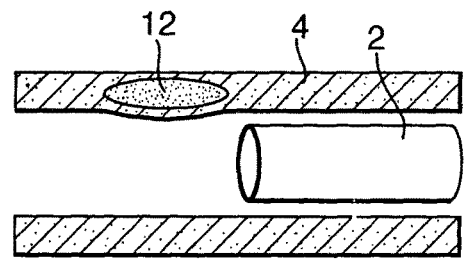
Figure 1D:
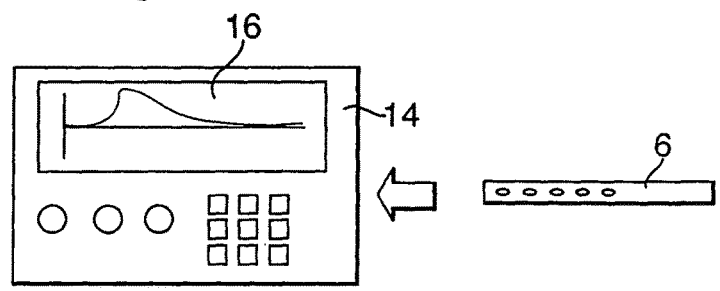
Figure 1E:
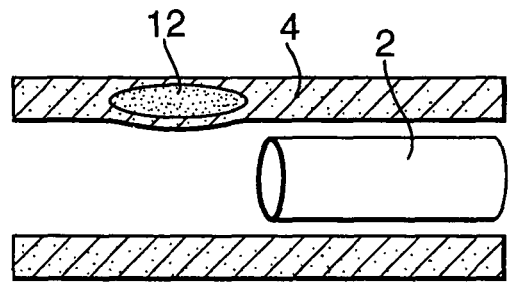
Figure 1F:
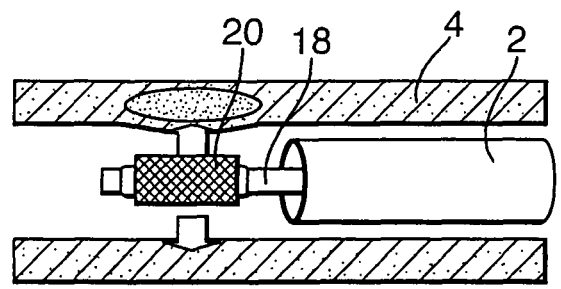
Figure 1G:
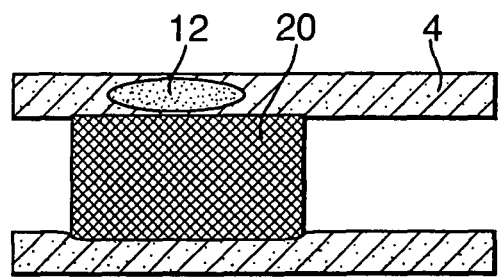

Methods of obtaining profiling data, diagnosis and treatment using a catheter of the present invention will be described with reference to the schematic representations given in FIG. 1(*a*) to (*g*).

As shown in FIG. 1, a reference guide (2) is inserted into a blood vessel (4) at a fixed position relative to the blood vessel (4). Then, as illustrated in FIG. 1(*b*) a sampling part (6) is inserted through an axial duct (8) of the reference guide (2). In the preferred embodiment, some form of indexing is provided such that, when fully inserted, the sampling part (6) has a predetermined relative positioning with the reference guide (2).

Various different embodiments will be described below, but, as illustrated in FIG. 1(*b*), the sampling part includes plurality of openings (10) for taking a plurality of blood samples along a length of the blood vessel (4) determined according to the position of the reference guide (2). As will be described below, the samples of blood taken by the opening (10) are used to identify a problem area in the blood vessel, such as plaque (12). The catheter need only be located in close proximity to a vessel wall (not in contact) and hence collect biological and chemical entities from very near the surface of the plaque. The sampling part (6) may be withdrawn from the reference guide (2) as illustrated in FIG. 1(*c*) and provided to an apparatus (14) as illustrated schematically in FIG. 1(*d*). The apparatus (14) analyses the blood samples and provides at an output a map of single/multiple biochemical marker gradients (16) along the length of the blood vessel (4). As illustrated in FIGS. 1(*e*) and (*f*), a treatment catheter (18) may then be deployed to the exact position of the zone of interest, e. g. vulnerable plaque, using the reliable positional reference of the reference guide (2) and using the information of the marker gradient from the apparatus (14).

In the example illustrated in FIGS. 1(*f*) and (*g*), the treatment catheter (18) deploys a localized drug delivery vehicle such as a drug-eluting stent. Those familiar with the state of the art in drug-eluting stents will recognize that this may be either a permanent or a transient biodegradable device.

It is also possible to provide a catheter of the present invention with an integrated treatment part which can be indexed to an appropriate position after diagnosis.

The present invention is applicable to observing not only biomarkers, where a biomarker can be considered a "biological entity that can give information regarding disease state", but also chemical entities e. g. Nitric Oxide that are also produced by those biological entities. Examples of biomarkers relevant to vulnerable plaque include:

CRP, PAPPA, Myeloperoxidase, MMP 9, sCD40L, PLGF, Neopterin, Soluble P-Selectin, sVCAM-1, sICAM-1, Soluble CD40L, VCAM-1, ICAM-1, P-Selectin, E-Selectin.

FIGS. 2(*a*), (*b*) and (*c*) illustrate schematically an example of a catheter arrangement useful for an understanding of the present invention.

The sampling part (6) includes a sample member (22) in which an axial array of a plurality of pockets (24) are formed. Each of the pockets (24) forms, at the outer surface of the sample member (22), a corresponding opening (26).

Sampling part (6) is also provided with an elongate sleeve (28) defining an axial passage (30) for housing the sample member (22). In this respect, FIGS. 2(*a*), (*b*) and (*c*) are highly schematic and the upstream end of the elongate sleeve (28) (to the left as illustrated) extends beyond the Figure. The sampling part (6) can be positioned as described with reference to FIGS. 1(*a*) to (*g*). With the sample member then in place, the sleeve (28) may be withdrawn from the sample member (22) as illustrated by arrow (32). The sleeve (28) includes a through hole (34). By withdrawing the sleeve (6) as illustrated in FIGS. 2(*b*) and (*c*), the through hole (34) moves in turn over each of the openings (26) so as to allow the respective pockets (24) to be filled with blood from outside the catheter.

A corresponding embodiment of the present invention is illustrated in FIGS. 2(*d*) and (*e*) where there is provided a plurality of through holes (35), in particular, a through hole (35) corresponding to each opening (26). In this case, the sleeve (28) is originally positioned such that all of its through holes are positioned adjacent parts of the sample member (22) where openings (26) are not provided. In this respect, they could be positioned radially or axially displaced from the openings (26). The sleeve (28) can then be moved so as to bring its through holes into alignment with the openings (26).

FIG. 3 illustrates a catheter like that illustrated in FIGS. 2(*a*), (*b*) and (*c*), but where the pockets (24) are evacuated prior to use. In other words, they have an internal pressure which is less than atmospheric and preferably significantly less than atmospheric.

When the sleeve (28) is moved to bring the through hole (34) adjacent the opening (26) of a pocket (24), the low pressure space thus draws in blood from outside the catheter. This helps prevent bubble release during collection and improves blood flow into the pocket.

In the arrangement of FIG. 4, instead of prior evacuation of the pockets (24), the pockets (24) are all interconnected by a vacuum passageway (36). The vacuum passageway (36) is connected to a source of suction such that when any through hole (34) connects a pocket (24) to the blood surrounding the catheter, blood is drawn into the pocket (24) as a result of the reduced pressure.

In the arrangement of FIG. 5, the pockets and, preferably, the vacuum passageway are pre-filled with a liquid, such as saline. Suction on the vacuum passageway withdraws the liquid from the pockets, such that they are replaced with blood from outside the catheter. The use of liquid (38) in this way helps prevent bubble release during collection.

Figure 6A:
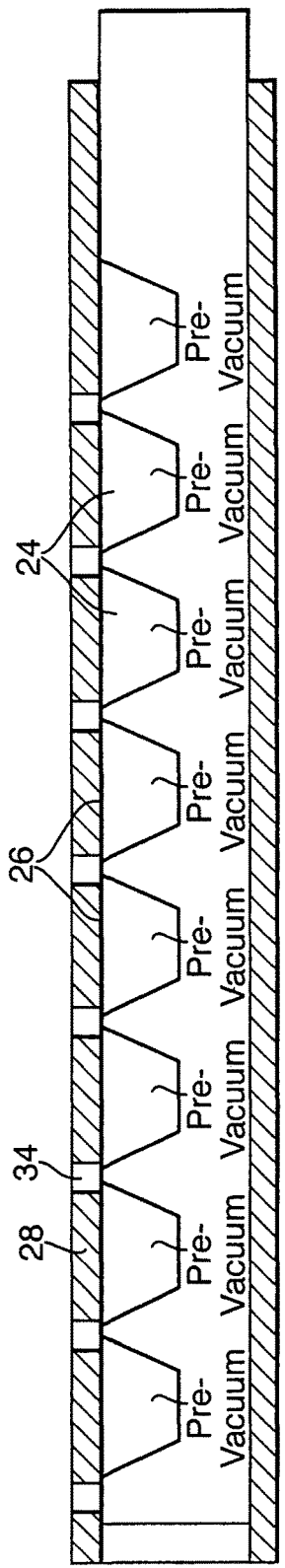
FIGS. 6(a) and (b) illustrate a catheter embodying the present invention.
Figure 6B:
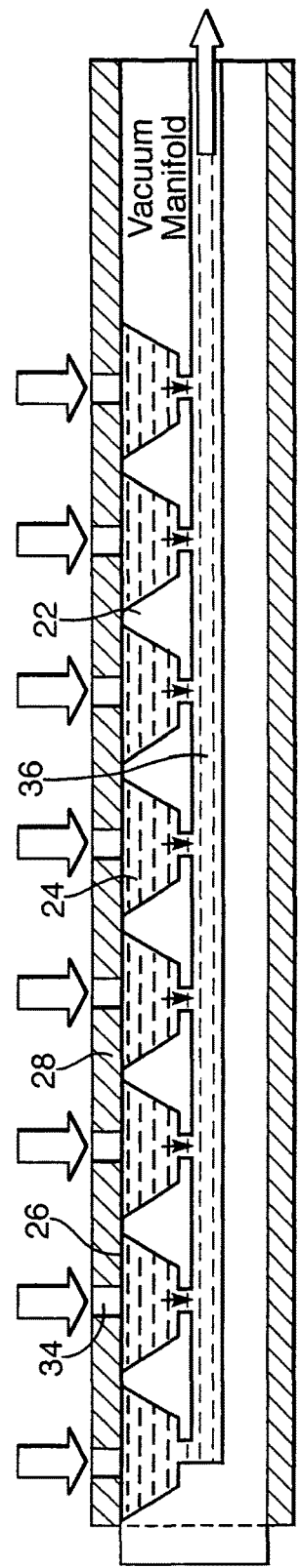

As mentioned above, the sleeve (28) can be provided with a plurality of through holes (34) corresponding to respective openings (26) and pockets (24). FIGS. 6(*a*) and (*b*) illustrate embodiments based on the arrangements of FIGS. 3 and 4 modified in this way. FIGS. 7(*a*) and (*b*) illustrate an embodiment based on the arrangement of FIG. 5 modified in this way.

Figure 8A:
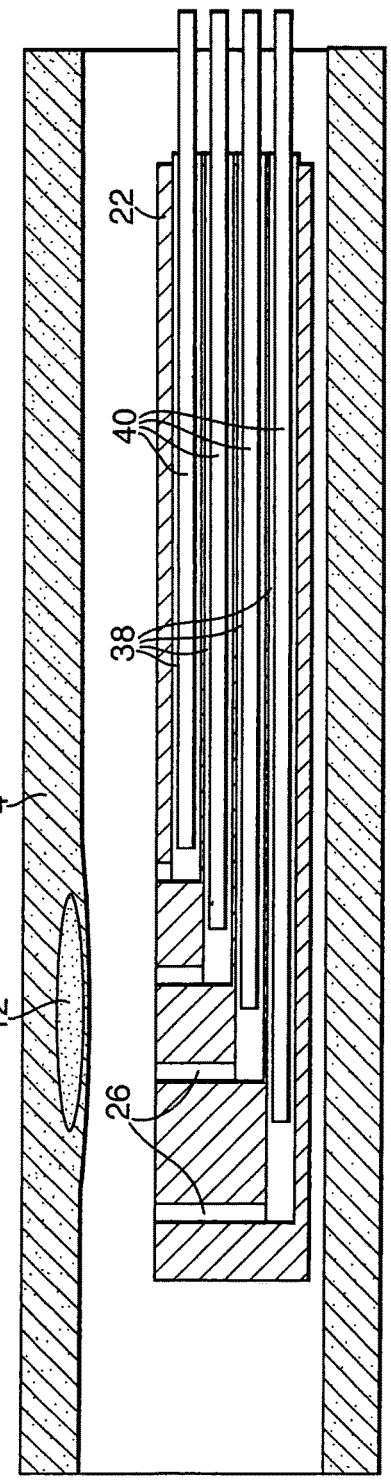
FIGS. 8(a) and (b) illustrate a catheter embodying the present invention.
Figure 8B:
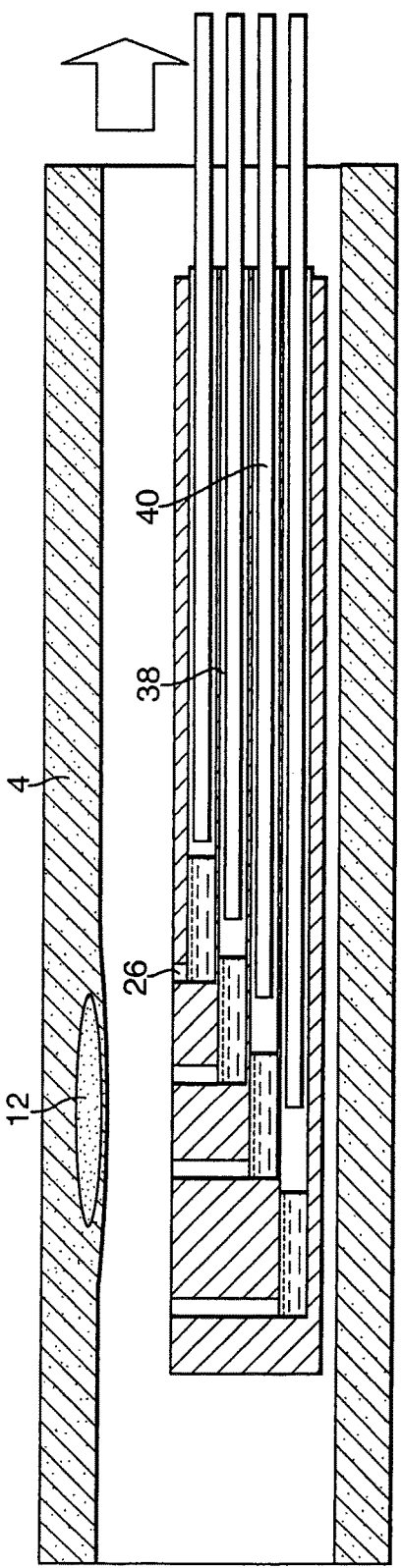

It is possible to use a plunger (40) in a vacuum passageway (38) in order to draw blood in through the openings (26). The embodiment of FIGS. 8(*a*) and (*b*) is based on an arrangement where individual respective vacuum passageways (38) are provided for each respective opening (26). As with the embodiments of FIGS. 4 and 5, an external vacuum source could be used to draw blood in through the openings (26). However, in the illustrated embodiment, respective plungers (40) are provided for each vacuum passageway (38). By withdrawing the plungers (44) away from the openings (26), samples of blood are drawn into the sample member (22) as illustrated in FIG. 8(*b*). Although individual pockets could be provided for each opening (26), in the illustrated embodiment, the vacuum passageways (38) effectively themselves form pockets. It will also be appreciated that, in this embodiment, a sleeve is not necessary, though, for certain applications, might be desirable.

In the embodiment of FIGS. 9(a) and (b), individual respective pistons (42) are provided in each pocket (24). Although arrangements are possible where the pistons (42) are movable individually, in the illustrated embodiment, all of the pistons are attached to an axially extending actuator (44). By moving the actuator (44) axially away from the far end of the catheter and, hence, away from the openings (26), blood is drawn into the pockets (24). The volumes of the pockets (24) prior to sampling can be evacuated prior to use so as to enable the pistons (42) to move. Alternatively, the pockets could be prefilled with a fluid which is driven out by the pistons (42) to an outlet channel or even to the blood vessel.

Rather than form individual pockets in the sample member (22), the sample member (22) can include a single continuous absorbent member which extends along the length of blood vessel to be diagnosed.

FIGS. 10(a) and (b) illustrate an embodiment with a single continuous absorbent member (46) within the sample member (22). In a manner similar to that described for the embodiment of FIGS. 7(a) and (b), the sleeve 28 with its through holes (34) can be moved from a position as illustrated in FIGS. 10(a) where the through holes (34) and openings (26) are not in alignment to a position as illustrated in FIG. 10(b) where they are in alignment. When the through holes (34) and openings (26) are in alignment, blood flows into the sample member (22) and is absorbed into the absorbent member (46) at predetermined positions along its length. Subsequently, samples can be taken from those predetermined positions. Also, the absorbent member (46) can be interrogated with micron resolution in an external device, for instance using fluorescent tags etc.

As illustrated in FIG. 11(a), the absorbent member (46) can comprise a planar member which is rolled into a cylinder and can then be unrolled as illustrated in FIG. 11(b). This provides additional three dimensional information because the sampling is being taken not only along the length of the blood vessel, but also at different radial angles around its periphery. As illustrated in FIGS. 11(a) and (b) the part (48) of the sample adjacent the problem area (12) will contain a variation, such as concentration, indicating the problem area (12). In this respect, the absorbent material can be interrogated with micron resolution in an external device, for instance fluorescent tags etc.

It will be appreciated that, although the embodiments described above have been described only with an axial array of openings and pockets, it is also possible to provide an array which additionally extends around the periphery of the catheter in a radial fashion. In this way, a three dimensional sample can be taken.

Figure 12:
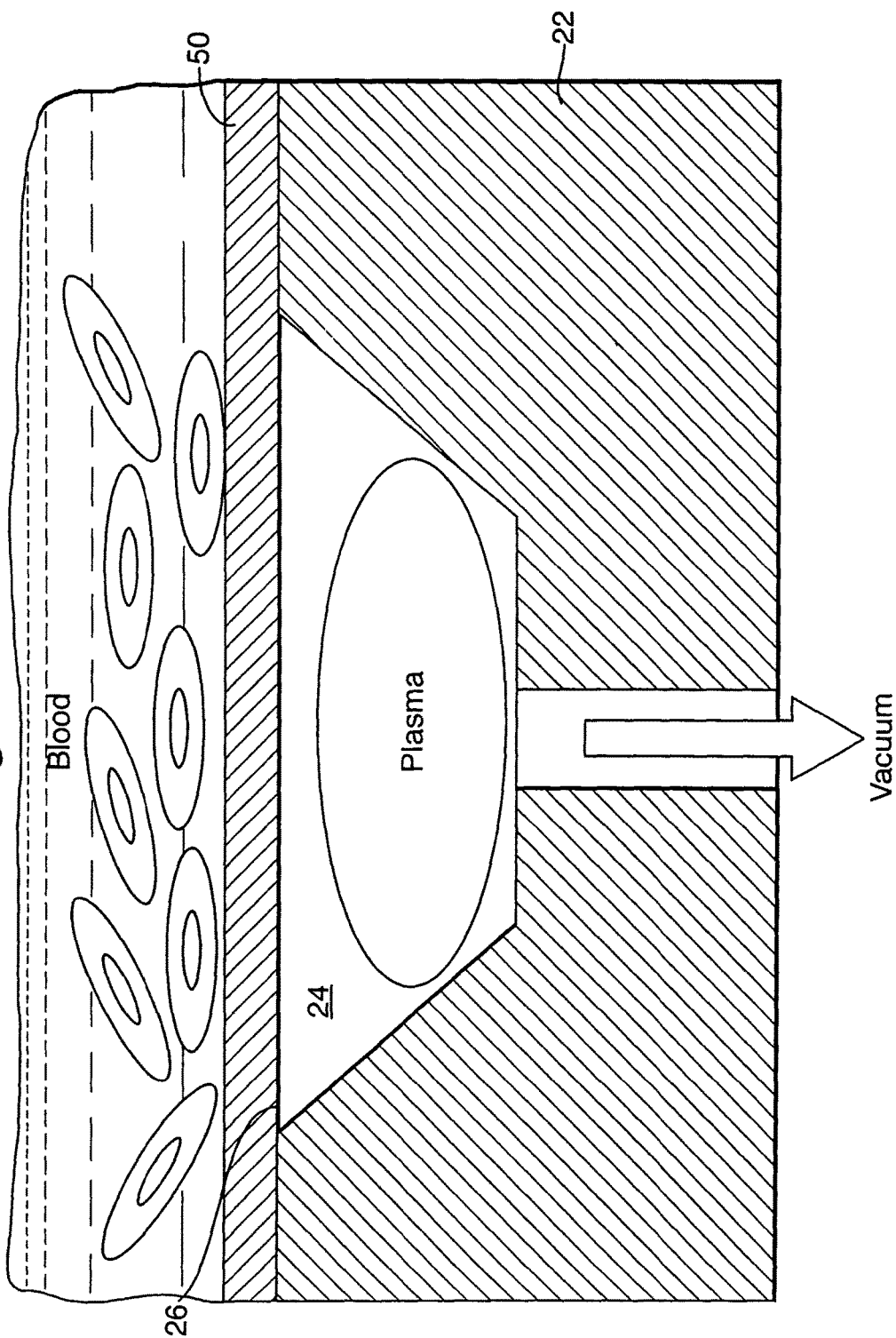
FIG. 12 illustrates a membrane for covering openings of catheters embodying the present invention.

As illustrated in FIG. 12, a membrane (50) may be used to cover the opening (26). This is also applicable where a pocket (24) is not used. The membrane allows plasma to pass through it, but not other parts of the blood. In this way, it increases the useful concentration of the test sample and, therefore, can reduce the required collection volume.

In one aspect of the invention as illustrated in FIGS. 13(a), (b) and (c), similar to the embodiment of FIGS. 11(a) and (b), a single continuous absorbent member (46) may be exposed in its entirety by withdrawing the sleeve (28). As a result, the blood absorbed into the absorbent member (46) represents a sample at a plurality of locations along the length of the blood vessel.

It is also possible to provide a suction tube in the centre of the absorbent member separated from the absorbent member by a membrane that allows air to pass through but not blood or biomarkers. This would help draw blood into the absorbent material but would prevent any pooling or mixing of the collected samples in the suction tube. A single suction tube can be provided like that illustrated in FIG. 4, 5, 6(b), 7(a) or 7(b). Alternatively, multiple tubes could be provided like those illustrated in FIGS. 8(a) and (b) or individual suction chambers like those illustrated in FIGS. 9(a) and (b).

It is also possible to capture a blood sample at a plurality of locations along the length of the blood vessel by using only a single opening or inlet port. FIGS. 14(a), (b) and (c) illustrate highly schematically a sampling part having an opening (26) forming an inlet port at a distal end and vacuum passageway (38) forming an axial channel running from the inlet port to a proximal end. By pulling the sampling part (6) along the length of the blood vessel (4) whilst applying suction to the axial channel at the outlet port, sequential slugs of blood may be sampled at known/positions. The resulting slugs of blood in the vacuum passageway (38) forming the axial channel represent a blood sample at plurality of locations along the length of the blood vessel. FIG. 15 illustrates schematically the positioning device (52) and suction device (54) required for this.

Blood contained in the vacuum passageway (38) forming the axial channel can then be dispensed into a sample collector having a plurality of discrete sample reservoirs. This is illustrated in FIG. 15 in relation to an embodiment where blood is sampled continuously and dispensed consecutively into sample reservoirs (56) of a sample collector (58). Of course, this is also preferably provided in conjunction with a positioning device.

The invention claimed is:

1. A catheter device for insertion into a blood vessel, comprising:
   a sampling part arranged to collect and preserve a plurality of spatially separated discrete blood samples from a plurality of locations along a length of the blood vessel;
   wherein the sampling part includes:
      an axially elongated sample member having an axial array of a plurality of openings for receiving blood from outside of the catheter device at intervals along the length of the blood vessel; and
      an elongated sleeve coaxial with the sample member, the sleeve defining an axial passage for housing the sample member and including a plurality of through holes corresponding to said openings in the sample member, and
   wherein movement between the sleeve and the sample member aligns all the through holes with the openings of the sample member, to simultaneously expose all the openings to blood outside the catheter device so as to collect the plurality of discrete blood samples along the length of the blood vessel, and
   wherein the catheter device is flexible so as to be channeled through the blood vessel, and has a blunt distal end.

2. The catheter device of claim 1, wherein the sampling part includes a plurality of pockets for receiving blood, with at least one pocket corresponding to each of said openings.

3. The catheter device of claim 2, wherein each of said plurality of pockets is at least partially evacuated, and
wherein alignment of the through holes with said openings draws blood from the outside of the catheter device into said pockets.

4. The catheter device of claim 2, wherein the sampling member further includes:
a vacuum passageway connecting each of said pockets, for applying suction to each of said pockets.

5. The catheter device of claim 4, wherein each of said connected pocket and vacuum passageway are pre-filled with a fluid that can be drawn out of the catheter device so as to draw blood from the blood vessel into each said pocket.

6. The catheter device of claim 1, wherein the sampling part includes a plurality of vacuum passageways connected to the plurality of openings, to allow suction to be applied to each of said openings.

7. The catheter device of claim 1, wherein the sampling part includes a plurality of vacuum passageways connected to the plurality of openings; and
wherein each of said openings is connected to an independent vacuum passageway from the plurality of vacuum passageways, to allow suction to be applied independently to each said opening.

8. The catheter device of claim 7, further comprising:
a plunger within each of the plurality of said vacuum passageway, each plunger being capable of moving in a direction away from its corresponding opening so as to draw blood in through the corresponding opening from the outside of the catheter device.

9. The catheter device of claim 2, wherein the sampling part further comprises within each of said pockets a moveable piston to draw blood through its corresponding opening into the pocket.

10. The catheter device of claim 9, wherein each piston is movable in an axial direction to suck blood into its respective pocket, and the sampling part further comprising an axially extending actuator to which all of the pistons are attached and by which the pistons may be cooperatively moved.

11. The catheter device of claim 2, further comprising: a membrane layer covering the pockets, the membrane layer allowing blood plasma into the pockets.

12. The catheter device of claim 1, wherein each said discrete blood sample is between 10 µl and 50 µl.

13. The catheter device of claim 1, wherein said sampling part includes a continuous absorbent material.

14. The catheter device of claim 1, wherein the sampling part is arranged to capture the plurality of discreet blood samples along the length of the blood vessel.

15. The catheter device of claim 1, wherein the openings of the sample member comprise an array of axially and radially spaced openings along the a length of the sample member.

16. A catheter system comprising:
(A) a catheter device for insertion into a blood vessel, the catheter device being flexible so as to be channeled through the blood vessel, and having a blunt distal end, comprising:
a sampling part arranged to collect and preserve a plurality of spatially separated discrete blood samples from a plurality of locations along a length of the blood vessel;
wherein the sampling part includes:
an axially elongated sample member having an axial array of a plurality of openings for receiving blood from outside of the catheter device at intervals along the length of the blood vessel; and,
an elongated sleeve coaxial with the sample member, the sleeve defining an axial passage for housing the sample member and including a plurality of through holes corresponding to said openings in the sample member, and
wherein movement between the sleeve and the sample member aligns all the through holes with the openings of the sample member, to simultaneously expose all the openings to blood outside the catheter device so as to collect the plurality of discrete blood samples along the length of the blood vessel; and
(B) an apparatus for analyzing discrete blood samples captured by the catheter device, the apparatus being capable of analyzing blood samples taken from the plurality of locations along said length of the blood vessel by providing a profile of concentration levels for one or more pathological markers in the samples taken along said length of the blood vessel.

17. The catheter system of claim 16, wherein the marker is an inflammatory marker.

18. The catheter system of claim 16, wherein the apparatus for analyzing is capable of calculating from the profile of concentration levels for the one or more pathological markers a background level of the one or more pathological markers in the blood samples.

19. The catheter system of claim 16, wherein the profile of concentration levels for the one or more pathological markers is displayed as a 2D map of the concentration levels of the one or more markers in a blood sample from the plurality of blood samples in relation to a location of said blood sample from the plurality of locations along the length of the blood vessel.

20. The catheter system of claim 16, wherein the sleeve and the sample member are configured so that the volume of each of the plurality of discrete blood samples is between about 10 µl and 50 µl.

* * * * *